US012672868B2

(12) United States Patent
Donners et al.

(10) Patent No.: US 12,672,868 B2
(45) Date of Patent: Jul. 7, 2026

(54) SUTURES WITH EXPANDED ANTIBACTERIAL PROPERTIES

(71) Applicant: Ethicon, Inc., Raritan, NJ (US)

(72) Inventors: Jackie J. Donners, Pennington, NJ (US); Howard Scalzo, Jr., Somerville, NJ (US); John Collier, Somerville, NJ (US); Vedanta Nayak, Raritan, NJ (US)

(73) Assignee: Ethicon, Inc., Raritan, NJ (US)

( * ) Notice: Subject to any disclaimer, the term of this patent is extended or adjusted under 35 U.S.C. 154(b) by 501 days.

(21) Appl. No.: 18/307,887

(22) Filed: Apr. 27, 2023

(65) Prior Publication Data

US 2024/0016491 A1 Jan. 18, 2024

Related U.S. Application Data

(60) Provisional application No. 63/336,543, filed on Apr. 29, 2022.

(51) Int. Cl.
| | |
|---|---|
| *A61B 17/06* | (2006.01) |
| *A61L 17/00* | (2006.01) |
| *A61L 17/12* | (2006.01) |
| *A61L 17/14* | (2006.01) |

(52) U.S. Cl.
CPC ...... *A61B 17/06166* (2013.01); *A61L 17/005* (2013.01); *A61L 17/12* (2013.01); *A61L 17/145* (2013.01); *A61L 2300/202* (2013.01)

(58) Field of Classification Search
CPC ...... A61L 17/12; A61L 17/005; A61L 17/145; A61L 2300/202; A61B 17/06166
See application file for complete search history.

(56) References Cited

U.S. PATENT DOCUMENTS

| | | | |
|---|---|---|---|
| 3,068,864 | A | 12/1962 | Hermann |
| 3,629,477 | A | 12/1971 | Model et al. |
| 3,767,362 | A | 10/1973 | Griffin et al. |
| 3,815,315 | A | 6/1974 | Glick |
| 3,839,297 | A | 10/1974 | Wasserman |
| 4,027,676 | A | 6/1977 | Mattei |
| 4,105,034 | A | 8/1978 | Shalaby et al. |
| 4,120,395 | A | 10/1978 | Mandel et al. |
| 4,126,221 | A | 11/1978 | Cerwin |
| 4,185,637 | A | 1/1980 | Mattei |
| 4,201,216 | A | 5/1980 | Mattei |
| 4,967,902 | A | 11/1990 | Sobel et al. |
| 5,128,101 | A | 7/1992 | Boynton |

(Continued)

FOREIGN PATENT DOCUMENTS

WO WO 2017/081692 A2 5/2017

OTHER PUBLICATIONS

International Search Report dated Aug. 8, 2023, for PCT application No. PCT/IB2023/054371.

(Continued)

*Primary Examiner* — Blessing M Fubara
(74) *Attorney, Agent, or Firm* — David R. Crichton; Leo B. Kriksunov

(57) ABSTRACT

The present invention is directed to coated medical devices, such as implantable and coatable devices, such as sutures, with expanded antibacterial properties, handling, knot slide and in-situ performance and processes for their manufacture and use.

28 Claims, 4 Drawing Sheets

(56) References Cited

U.S. PATENT DOCUMENTS

| 5,213,210 | A | | 5/1993 | Cascio et al. | |
|---|---|---|---|---|---|
| 5,230,424 | A | | 7/1993 | Alpern et al. | |
| 5,464,580 | A | | 11/1995 | Popescu et al. | |
| 5,555,976 | A | | 9/1996 | Pernot | |
| 5,868,244 | A | | 2/1999 | Ivanov et al. | |
| 5,972,008 | A | | 10/1999 | Kalinski et al. | |
| 6,260,699 | B1 | | 7/2001 | Kaplan et al. | |
| 8,273,104 | B2 | * | 9/2012 | Cohen | A61L 17/145 |
| | | | | | 606/228 |
| 2005/0149119 | A1 | | 7/2005 | Koyfman et al. | |
| 2012/0277772 | A1 | * | 11/2012 | Aben | C08L 23/06 |
| | | | | | 606/228 |
| 2013/0193008 | A1 | | 8/2013 | Reyhan et al. | |
| 2018/0325943 | A1 | * | 11/2018 | Loitner | A61L 17/145 |

OTHER PUBLICATIONS

Written Opinion issue dated Aug. 8, 2023, for PCT application No. PCT/IB2023/054371.

* cited by examiner

Scatterplot ZOI vs triclosan density in coating

Scatterplot of Day-3 ZOI [mm] vs Triclosan Density in Coating [ug/mm3]

SUTURES WITH EXPANDED ANTIBACTERIAL PROPERTIES

PRIORITY CLAIM

The present application claims priority to U.S. Provisional Patent Application Ser. No. 63/336,543 filed Apr. 29, 2022; the disclosure of which is incorporated herewith by reference.

TECHNICAL FIELD

The present invention is directed to sutures with expanded antibacterial properties, good handling, knot slide and in-situ performance and processes for their manufacture and use.

BACKGROUND

Sutures having anti-microbial properties against one or more species of bacteria are known. One class of sutures with anti-microbial properties have incorporated triclosan onto the suture. There is a desire to increase the anti-microbial efficacy of sutures against additional bacterial species compared to the currently available antimicrobial braided sutures. Specifically, *Escherichia coli* (*E. coli*), *Klebsiella pneumoniae* (*K. pneumoniae*) and *Enterobacter cloacae* (*E. cloacae*). Of these species, *E. cloacae* requires the highest concentration of antimicrobial to inhibit bacterial growth. Thus, if efficacy against *E. cloacae* is demonstrated, efficacy against the other species should be obtained as well. Increasing triclosan content on sutures creates new challenges however as high triclosan content negatively impacts suture handling, especially the ability to slide down a square knot into the locking knot. Suture coatings for antimicrobial sutures require a coating component that can absorb the antimicrobial and a coating component that provides lubricity. In some cases, a component can provide both functions.

Current braided antimicrobial suture processes introduce triclosan to sutures via coating solutions. The challenges of this technology are two-fold: There is a practical limit in terms of triclosan solubility in the coating solution and during sterilization and hot room treatment, most of the triclosan coated on the suture will volatilize and transfer from the suture to the surrounding package. For example, the resulting concentration of triclosan on sutures of finer sizes within certain package types is less than that needed to be sufficiently effective against certain strains of bacteria such as *E. cloacae*.

SUMMARY OF THE INVENTION

Applicants discovered that good antimicrobial efficacy and good suture handling requires a balance of triclosan content, coating add on/thickness on the suture and the ratio of coating components if more than one component is used in the coating. More specifically, if triclosan content is too low there is no antimicrobial efficacy but for a given coating system above certain triclosan thresholds one cannot provide sufficient coating volume to accommodate the triclosan without negatively impacting handling. Both knot slide and zone of inhibition, which is elution driven, correlate well with triclosan density in the coating (e.g. micrograms of triclosan per cubic millimeter of coating), whereas attachment driven efficacy, such as bacterial colonization, correlate well with normalized triclosan content per meter of suture (micrograms per meter) across suture sizes.

DETAILED DESCRIPTION

There is a desire to increase the triclosan content on antimicrobial braided sutures to achieve efficacy against additional bacterial species compared to those current commercial antimicrobial braided sutures are effective against. Specifically, *Escherichia coli* (*E. coli*), *Klebsiella pneumoniae* (*K. pneumoniae*) and *Enterobacter cloacae* (*E. cloacae*). Of these species, *E. cloacae* requires the highest antimicrobial dose and thus if efficacy against *E. cloacae* is demonstrated, efficacy against the other species should be obtained as well.

Figure 1:
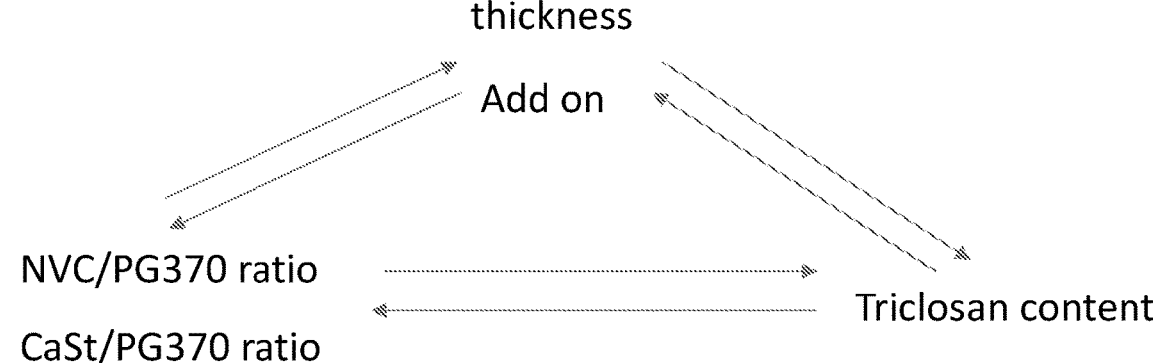
FIG. 1 is a diagram that illustrates the relationship of factors for securing antimicrobial efficacy and suture handling.

Increasing triclosan content on sutures creates new challenges however, as high triclosan content negatively impacts suture handling, especially the ability to slide down a square knot into the locking knot. Suture coatings for antimicrobial sutures require a coating component that can absorb the antimicrobial; i.e., triclophilic), and a coating component that provides lubricity. In some cases, a component can provide both functions. It turns out that enhanced antimicrobial efficacy and good suture handling requires a balance of triclosan content, coating add on/thickness on the suture and the ratio of lubricious and triclophilic coating components if more than one component is used in the coating (FIG. 1).

More specifically, if the triclosan content is too low there is no antimicrobial efficacy but for a given coating system above certain thresholds one cannot provide sufficient coating volume to accommodate the triclosan without negatively impacting handling. Both knot slide and zone of inhibition, which is elution driven, correlate well with triclosan density in the coating (e.g. micrograms of triclosan per cubic millimeter of coating), whereas attachment driven efficacy such as bacterial colonization generally correlate well with normalized triclosan content per meter of suture (micrograms per meter) across suture sizes.

The following terms and definitions are provided for purposes of this application:

PCG is a low crystalline, low molecular weight poly (caprolactone-co-glycolide) material in random or block polymer form.

NVC means a PCG with a target monomer unit ratio of 90/10 (90% caprolactone and 10% glycolide).

NVC (wt %) means the weight percent of NVC in a solution used that is used to coat a suture.

PCL is a low crystalline, low molecular weight poly (caprolactone-co-lactide) material in random or block copolymer form.

PLG is a low crystalline, low molecular weight poly (glycolide-co-lactide) material in block or random polymer form.

PG370 is PLG with a target monomer unit ratio of 65/35 (65% glycolide and 35% lactide)

CaSt (wt %) means the weight percent of calcium stearate in a solution that is used to coat a suture.

Triclosan in Coating Solution (wt %) means the weight percent of triclosan in a solution that is used to coat a suture.

Triclosan Reservoir Dose (mg) means the mass of triclosan contained within a package.

Triclosan Content (ug(micrograms)/m) means the total mass in micrograms of triclosan resident on a one meter length of suture.

Triclosan Density in the Coating (ug(micrograms)/mm³) means the mass in micrograms of triclosan per cubic millimeter of dry coating on suture.

Coating Add On (wt %) means the weight percent of the coating on a suture (i.e., the mass of the coating as a percentage of the total mass of the coating and suture).

Knot Slide (N/m) means the normalized area under the force-extension curve when pulling on two ends of a suture to slide a square knot formed between the two ends of the suture to the closed position normalized to the distance of travel.

TSB means tryptic soy broth, a bacterial growth medium.

SST stands for Serum:Saline:TSB and % value typically refers to volume of Serum to the overall volume. TSB concentration is always at 10 percent volume for the present invention and saline:serum ratio changes with serum concentration. Phosphate buffer can be used instead of saline at similar concentrations.

TSA means tryptic soy agar, a bacterial growth medium.

Colony-forming-unit (CFU) is a unit of measure for estimating the number of viable microbial cells in a sample. The CFU is measured visually using viable plate counts. The purpose of plate counting is to estimate the number of cells present based on their ability to give rise to colonies under specific conditions of nutrient medium, temperature, and time. Theoretically, one viable cell can give rise to a colony through replication.

ZOI typically refers to Zone of Inhibition after 24 hours.

ZOI Day 3 (mm) means the Zone of Inhibition measured in millimeters (mm) as measured after 72 hours of incubation wherein the suture was transferred into a fresh agar plate each 24 hours.

Log Reduction means a logarithmic reduction in attached bacteria to the triclosan containing suture compared to a control suture. Unless specified otherwise, results are after 24 hours of incubation.

Triclosan Reservoir means a component that is able to contain a specific quantity of triclosan as source of transfer to the medical device.

Plastic means a package tray made from a resin of polypropylene or high-density polyethylene.

Paper means a paper folder made from either a coated (clay-based coating) or un-coated paper.

Vapor Process means the transfer of triclosan from the Triclosan Reservoir to the medical device at temperature, time and/or reduced pressure.

In one embodiment, the present invention is directed to medical device coating compositions applied onto a medical device that is a coating with a quantity per length containing triclosan, a triclophilic component and a lubricious component. The triclosan content in the coating is between about 150 micrograms/meter and about 2500 micrograms/meter for improved antimicrobial efficacy including >3 log reduction of bacteria and extended antimicrobial efficacy (both ZOI and log reduction for at least 3 days). The triclosan density in the coating can be between about 40 micrograms/mm³ and about 1000 micrograms/mm³ of coating for improved knot slide, ZOI efficacy, and duration. The medical device coating composition means a coating that has been applied on the medical device after any solvent or other carrier used in the coating process has been removed. The medical device coating composition refers to coating as found on the suture in finished form.

Examples of preferred absorbable medical devices include mono and multifilament sutures. The multifilament suture includes sutures wherein a plurality of filaments are formed into a braided structure. Examples of non-absorbable medical devices include mono and multifilament sutures, surgical meshes such as hernia repair mesh, hernia plugs and brachy seed spacers, which may be polymeric or nonpolymeric. In one embodiment, the suture is selected from the group of braided, monofilament, twisted suture and barbed. The different types of sutures, including braided, monofilament, and barbed suture, can use a variety of materials, including polylactide co-glycolide, (e.g., Coated VICRYL®) (polyglactin 910) Suture), polycaprolactone-co-glycolide (e.g., MONOCRYL® (poliglecaprone 25) Suture), polydioxanone (e.g., PDS® II (polydioxanone) Suture), poly-caprolactone-co-lactide, polyglycolide, polylactide, poly L-lactide, polycaprolactone, polyglycolide-co-trimethylene carbonate, polytrimethylene carbonate, surgical gut, polyester (e.g., ETHIBOND EXCEL® Polyester Suture), silk (e.g. PERMA-HAND® Silk Suture), polypropylene (e.g., PROLENE® Polypropylene Suture), other absorbable or non-absorbable materials, and the like. In one embodiment, the suture is a coated multi-filament suture of polyglactin 910 (PG910) commercially available from Ethicon under the tradename Coated VICRYL Suture.

Sutures are provided in a variety of industry conventional sizes using the size system identified in the currently recognized United States Pharmacopoeia (USP) that, for absorbable sutures, can range from USP size 11/0 to USP size 7. USP 4/0 sutures have a diameter of about 0.15 mm. USP 3/0 sutures have a diameter of about 0.2 mm. USP 2/0 sutures have a diameter of about 0.3 mm. USP Size 0 sutures have a diameter of about 0.35 mm. In one embodiment, the weight percent of the coating to suture weight is between 0.5% and 8% for a 2/0 suture.

Suitable antimicrobial agents may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477, which is incorporated herein by reference.

One particularly preferred antimicrobial agent is 2,4,4'-trichloro-2'-hydroxydiphenyl ether, commonly referred to as triclosan, a material that is commercially available from various sources. Triclosan is a broad-spectrum antimicrobial agent that has been used in a variety of products, and is effective against a number of organisms commonly associated with SSIs. Such microorganisms include, but are not limited to, *Staphylococcus epidermidis, Staphylococcus aureus*, methicillin-resistant *Staphylococcus epidermidis*, methicillin-resistant *Staphylococcus aureus, Enterobacter cloacae, Klebsiella pneumoniae, Escherichia coli* and combinations thereof.

A triclophilic component is a material that readily absorbs or has high affinity for triclosan. It is advantageous to use a triclophilic containing coating composition as a vehicle for delivering the antimicrobial agent to the surface of the device where such coating already is used conventionally in the manufacture of the device, such as, for example, absorbable and non-absorbable multifilament sutures. Examples of medical devices, as well as coatings that may be applied thereto, may be found in U.S. Pat. Nos. 4,201,216, 4,027, 676, 4,105,034, 4,126,221, 4,185,637, 3,839,297, 6,260,699, 5,230,424, 5,555,976, 5,868,244, and 5,972,008, each of which is hereby incorporated herein in its entirety. As disclosed in U.S. Pat. No. 4,201,016, suitable coating composition may include a film-forming polymer and a substantially water-insoluble salt of a C6 or higher fatty acid as a lubricious agent. As another example, an absorbable coating composition that may be used for an absorbable medical device may include poly(alkylene oxylates) wherein the alkylene moieties are derived from C6 or mixtures of C4 to C16 diols, which is applied to a medical device from a solvent solution, as disclosed in U.S. Pat. No. 4,105,034. The coating may be applied to the device by, for example, dip coating, spray coating, suspended drop coating, or any other conventional coating means. PCG or PCL, preferably NVC, and PLG, preferably PG370 as provided in the coating component on a device as described herein are suitable triclophilic materials.

In order to enable sufficient uptake of antimicrobial agent, a minimal amount of triclophilic component in the coating is required. The amount required depends on the relative triclophilicity of the component. In the present invention, NVC has a higher affinity for triclosan than PG370 and thus sufficient amounts of antimicrobial agent can be achieved at a lower amount of NVC than for PG370. Moreover, the relative triclophilicity of the coating can be fine-tuned by using combinations of triclophilic components.

Lubricous components can be provided in the coating solutions and remain in the resulting coating compositions. As noted above, calcium stearate and PCG, preferably NVC are examples of suitable lubricious components. The lubricous component can be provided from the PCG or PCL, preferably NVC coating from an PCG, moreover NVC-containing solution can optionally further comprise calcium stearate.

Coatings can either be substantially homogeneous or heterogeneous in nature. In the case of a homogeneous coating, the coating components are chemically similar enough that they are able to mix on a molecular level. In the case of a heterogeneous coating the coating components do not fully mix at the molecular level and micro domains of the components can form.

In one embodiment of the present invention, NVC is both the triclophilic and lubricious component and PG370 is optionally included to modulate suture handling properties. In order to achieve sufficient triclosan for antimicrobial properties a total amount of triclophilic component from about 0.5 to 8 percent by weight to the mass of a size 2-0 suture is preferred, an amount of about 1 to 6 percent by mass is more preferred and an amount of about 1.5 to 5 percent by mass is most preferred. Required coating weight percents will be slightly different for different suture sizes. In another embodiment, in order to achieve sufficient triclosan for antimicrobial properties a total amount of triclophilic component from about 4 to 10 percent by weight to the mass of a size 4-0 suture is preferred, an amount of about 4.5 to 9 percent by mass is more preferred and an amount of about 5 to 8 percent by mass is most preferred. In order to sustain proper suture handling properties for these substantially homogeneous coatings, triclosan concentration in the coating needs to be limited to an upper limit of about 1000 micrograms triclosan per cubic millimeter of coating, more preferably to an upper limit of 400 micrograms triclosan per cubic millimeter of coating and most preferably to an upper limit of 300 micrograms triclosan per cubic millimeter of coating. Similarly, a certain minimum thickness of coating is required to effectively mask the braid surface and obtain proper suture handling properties, whether triclosan is present or not. The lubricious component being the dominant component in the coating is the preferred method to fine tune suture handling properties. In this embodiment, an NVC to PG370 ratio greater than 1 is preferred, a ratio of greater than 2 is more preferred and a ratio of greater than 3 is most preferred. Inclusion of the less triclophilic component PG370 is another method to control suture handling properties by limiting the amount of triclosan that is present in a given coating amount. Moreover, small amounts of calcium stearate or other lubricious components can be optionally included to further fine tune properties.

In another embodiment, a coating solution for use in coating a suture of the present invention selected from USP size 2 through 3-0 comprises about 3 weight percent to at least about 8 weight percent of PCG, preferably NVC, and about 0 to about at least 6 weight percent PLG, preferably PG370, preferably from about 4 weight percent to about 8 weight percent of PCG, preferably NVC, and from about 0 to about 4 weight percent of PLG, preferably PG370. The PCG, preferably NVC, acts as both triclophilic and lubricious agents, while the polymer components of PLG, preferably PG370 are capable as acting as the triclophilic agent.

In another embodiment of the present invention, the triclophilic component is PG370 and the lubricious component is calcium stearate. In this case, the nature of the coating is heterogeneous. In order to achieve sufficient triclosan for antimicrobial properties a total amount of triclophilic component from about 0.6 to 2 percent by weight to the mass of a size 2-0 suture is preferred, an amount of about 1 to 1.7 percent by mass is more preferred. Required coating weight percents will be slightly different for different suture sizes. In order to sustain proper suture handling properties, for this embodiment controlling the lubricious to triclophilic component is important. Suture handling properties can deteriorate rapidly once the triclophilic component is the dominant component and having an excess of lubricious component is preferred.

In another embodiment, a coating solution for use in coating a suture of the present invention comprises about 3 weight percent to at least about 6 weight percent of calcium stearate and about 3 to about at least 6 weight percent PLG, preferably PG370, preferably from about 4.5 weight percent to about 6 weight percent of calcium stearate and from about 4.5 to about 6 weight percent of PLG, preferably PG370. The calcium stearate acts as the lubricious agent, while the polymer components of PLG, preferably PG370 are capable as acting as the triclophilic agent.

PCG or PCL coating solutions contain diluted copolymers of epsilon-caprolactone and glycolide that are formed by using glycolic acid as an initiator and stannous octoate as the catalyst. The polymerization may be conducted in a batch process that allows the formation of a random copolymer. However, it is also possible to conduct the polymerization in such a way as to allow for the formation of a semi-block copolymer. The initiator ratio may be varied to allow one to obtain a molecular weight that makes the final copolymer in a useable form. The term "initiator ratio" as used herein, refers to the total moles of monomer divided by the total moles of initiator.

Suitable film formers for use as alternatives to the PLG component coating compositions of this invention include homopolymers and copolymers of lactide and glycolide, i.e., polylactide, polyglycolide, and copolymers of lactide and glycolide with each other and with other reactive monomers; poly(p-dioxanone), poly(alkylene oxalate), copolymers of vinyl acetates with unsaturated carboxylic acids such as crotonic, acrylic, and methacrylic acids; water soluble or dispersible cellulose derivatives such as methyl cellulose, hydroxymethyl cellulose and carboxymethyl cellulose; natural gums; ethylene oxide polymers; polyacrylamide; collagen; gelatin; polyamino acids; polyvinyl alcohol; polyvinyl pyrrolidone; polyoxaesters; polybutilate; absorbable conjugated unsaturated triglycerides such as dehydrated castor oil, and mixtures of such polymers. Particularly preferred film-forming polymers are the copolymers of lactide and glycolide which are low molecular weight and exhibit no or low levels of crystallinity. These polymers are water-insoluble, rapidly absorbable, and soluble in many common organic solvents such as acetone, chloroform, toluene, xylene, and 1,1,2-trichloroethane which facilitates their application to the suture as solutions.

In addition to PCG and PLG coatings, other suitable coatings can include, but not limited to polyglyconate, a copolymer of glycolic acid and trimethylene carbonate and copolymer coatings containing caprolactone with an ester of a fatty acid. Mixtures useful in forming such coatings include an ester of a fatty acid as a predominant component. The minor component of such mixtures comprises copolymers containing caprolactone. Examples of useful caprolactone containing copolymers are "star" copolymers obtained by polymerizing a major amount of epsilon-caprolactone and a minor amount of another bioabsorbable monomer polymerizable therewith in the presence of a polyhydric alcohol initiator. Suitable monomers which can be copolymerized with epsilon-caprolactone include alkylene carbonates such as trimethylene carbonate, tetramethylene carbonate, dimethyl trimethylene carbonate; dioxanones; dioxepanones; absorbable cyclic amides; absorbable cyclic ether-esters derived from crown ethers; hydroxyacids capable of esterification, including both alpha hydroxy acids (such as glycolic acid and lactic acid) and beta hydroxyacids (such as beta hydroxybutyric acid and gamma hydroxyvaleric acid); polyalkyl ethers (such as polyethylene glycol and polyloropyline glycol and combinations thereof; with glycolide being a preferred monomer. Examples of useful fatty acid esters include calcium stearolyl lactylate, which is soluble in the copolymer solution.

In one embodiment of the packaged antimicrobial medical device includes at least one package having an inner surface with an antimicrobial agent disposed thereon, the antimicrobial agent being selected from halogenated hydroxyl ethers, acyloxydiphenyl ethers, and combinations thereof described above, in an amount sufficient to substantially inhibit bacterial colonization on the package; and at least one medical device positioned within the package, the medical device having one or more surfaces having an antimicrobial agent disposed thereon and therein, the antimicrobial agent being selected from halogenated hydroxyl ethers, acyloxydiphenyl ethers, and combinations thereof, in an amount sufficient to substantially inhibit bacterial colonization on the medical device.

Another embodiment of the packaged antimicrobial medical device includes a package having an inner surface and a containment compartment for securing the medical device and that resides within the package. In this embodiment, at least one surface of the containment compartment includes an antimicrobial agent disposed thereon, present in an amount sufficient to substantially inhibit bacterial colonization on the containment compartment. In an alternate embodiment, the inner surface of the package and at least one surface of the containment compartment include an antimicrobial agent disposed thereon, present in an amount sufficient to substantially inhibit bacterial colonization on the package and the containment compartment. The packaged medical device also includes at least one medical device positioned within the containment compartment. The medical device also has one or more surfaces having an antimicrobial agent disposed thereon. The antimicrobial agent is present on the medical device in an amount sufficient to substantially inhibit bacterial colonization on the medical device. The antimicrobial agent disposed on the package, the containment compartment and medical device may be selected from antimicrobial compounds which include halogenated hydroxyl ethers, acyloxydiphenyl ethers, and combinations thereof.

Packages for surgical needles, sutures and combinations including the suture and a surgical needle typically comprise a suture tray as the containment compartment, for securely holding the suture and/or surgical needle in place. One type of containment compartment typically used for surgical needles and/or sutures is a folder package made from a stiff, medical grade paper. A folder package will typically have a plurality of foldable panels and cut-out tabs and tab pockets. Folder packages for surgical needles and sutures are illustrated and disclosed in the following patents, each of which is hereby incorporated by reference in its entirety: U.S. Pat. Nos. 4,126,221, 4,120,395 and 5,555,976.

Another conventionally used containment compartment for surgical needles and/or sutures is a molded plastic tray having a central floor surrounded by an outer winding channel for receiving and retaining a suture, e.g., an oval channel, the containment compartment may further include a medical grade paper or plastic cover that may be mounted to the top of the winding channel, or the molded plastic tray may have molded retainer elements, in order to maintain the suture in the channel. molded thermoplastic material. The molded plastic tray may be made from a thermoplastic material selected from the group consisting of polyester, polyvinyl chloride, polypropylene, polystyrene, and polyethylene. Containment compartments having winding channels are illustrated in the following, each of which is hereby incorporated by reference in its entirety: U.S. Pat. Nos. 4,967,902, 5,213,210 and 5,230,424.

The present invention is also directed to a method for preparing a packaged antimicrobial medical device, which includes the steps of providing a package and/or a containment compartment that is substantially free of an antimicrobial agent; positioning a medical device within the package or the containment compartment, the medical device including one or more surfaces having an antimicrobial agent disposed thereon, the antimicrobial agent being selected from the group consisting of halogenated hydroxyl ethers, acyloxydiphenyl ethers, and combinations thereof, subjecting the package and/or the containment compartment and the medical device to conditions sufficient to transfer a first portion of the antimicrobial agent from the medical device to the package and/or the containment compartment, while retaining a second portion of the antimicrobial agent on the surface of the medical device, thereby substantially inhibiting bacterial colonization on the medical device, the package and/or the containment compartment.

In accordance with various methods of the present invention, in one embodiment, a package and containment compartment that are initially substantially free of an antimicrobial agent, i.e., no antimicrobial agent is intended to be present on the package or containment compartment surfaces, may be provided. A medical device, which has a preselected amount of an antimicrobial agent disposed thereon, is positioned within the package or containment compartment. Subsequently, the package, the containment compartment if utilized and the medical device are subjected to preselected time, temperature and pressure conditions sufficient to vapor transfer a portion of the antimicrobial agent from the medical device to the package and/or the containment compartment.

The rate of transfer of an antimicrobial agent such as triclosan from the medical device to the package and/or containment compartment is substantially dependent upon the time, temperature and pressure conditions under which the package with the containment compartment and the medical device is stored and handled. Also included are any combinations of pressure and temperature to render a partial pressure for the antimicrobial agent that is the same as the partial pressure rendered under the conditions described above, in combination with a period of time sufficient to render an effective amount or concentration of the antimicrobial agent on the package and/or containment compartment. Specifically, it is known to one of ordinary skill that if the pressure is reduced, the temperature may be reduced to achieve the same partial pressure. Alternatively, if the pressure is reduced, and the temperature is held constant, the time required to render an effective amount or concentration of the antimicrobial agent on the package and/or containment compartment may be shortened. While a portion of the antimicrobial agent is transferred to the package and/or containment compartment during this process, a second portion is retained on the surface of the medical device. Accordingly, after the transfer, the medical device and the package and/or the containment compartment contain the antimicrobial agent in an amount effective to substantially inhibit bacterial colonization thereon and thereabout.

Medical devices typically are sterilized to render microorganisms located thereon non-viable. In particular, sterile is understood in the field of art to mean a minimum sterility assurance level (SAL) of $10^{-6}$. Examples of sterilization processes are described in U.S. Pat. Nos. 3,815,315, 3,068, 864, 3,767,362, 5,464,580, 5,128,101 and 5,868,244, each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

In one embodiment, an ethylene oxide sterilization process is utilized to transfer the volatile antimicrobial agent, for example triclosan, since the time, temperature and pressure conditions of the sterilization process are sufficient to vapor transfer a portion of the antimicrobial agent from the medical device to the package and/or containment compartment. However, many ethylene oxide sterilization processes exist with different time, temperature and pressure conditions, which in turn provide more or less vapor transfer of the antimicrobial agent.

In another embodiment, a pre-sterilization treatment of the medical device, for example placing in a vacuum oven, can provide the time, temperature and pressure conditions to provide sufficient vapor transfer of the antimicrobial agent to the medical device from the package and/or containment compartment and then sterilized in a subsequent step.

In another embodiment, a post-sterilization treatment of the sterilized medical device, for example placing in a vacuum oven, can provide the time, temperature and pressure conditions to provide sufficient vapor transfer of the antimicrobial agent to the medical device from the package and/or containment compartment.

It is known to those skilled in the art that any combination of the above three embodiments can be utilized.

In one embodiment, the present invention is directed to methods of introducing an antimicrobial agent, such as triclosan, into the coated suture by exposing the suture to patches having a reservoir of triclosan, wherein the transfer occurs under raised temperature and/or reduced pressure.

In one embodiment, the present invention is directed to methods of introducing an antimicrobial agent, such as triclosan, into the coated suture by exposing the suture to a reservoir of triclosan located within trays, wherein the transfer occurs under raised temperature and/or reduced pressure. In another embodiment, the triclosan is embedded in the tray and transferred to the suture under raised temperature and/or reduced pressure.

In one embodiment, the present invention is directed to a coated braided suture having a triclosan content on the suture greater than 150 µg/m and a triclosan density in the coating greater than 70 µg/mm³, more preferably greater than 85 µg/mm³, most preferably greater than 100 ug/mm³ and sustains >3 mm Zone of Inhibition against *E. cloacae* for at least 3 days.

In one embodiment, the present invention is directed to a coated braided suture having a triclosan content in the coating greater than 150 µg/m, more preferably greater than 200 µg/m and exhibits greater than 3 log reduction in bacterial attachment of *E. cloacae* relative to a non-triclosan containing suture of the same chemical nature, architecture, and size in the presence of 20% serum. The magnitude of the reduction is depending both on triclosan content on the suture and the amount of serum present in the bacterial growth medium. As a rule of thumb, smaller log reductions are observed with increased serum content and larger reductions with increased triclosan content. In another embodiment, the present invention is directed to a coated braided suture having an initial triclosan content on the suture greater than 200 µg/m, more preferably greater than 250 µg/m, most preferably greater than 300 µg/m and exhibits greater than 3 log reduction in bacterial attachment of *E. cloacae* relative to a non-triclosan containing suture of the same chemical nature, architecture, and size for 2 days. In another embodiment, the present invention is directed to a coated braided suture having an initial triclosan content on the suture greater than 300 µg/m, wherein coating thickness exceeds 2 micrometer, more preferably exceeds 2.5 micrometer, and exhibits greater than 3 log reduction in bacterial attachment of *E. cloacae* relative to a non-triclosan containing suture of the same chemical nature, architecture, and size for 3 days.

In one embodiment, the present invention is directed to a coated braided suture of USP size 4/0 through 0 as described above having a quantitative knot slide value of less than 60 N/m, preferably less than 30 N/m, most preferred less than 20 N/m.

In one embodiment, the coated braided suture USP size is between and including 0 to 4/0.

EXAMPLES

Example 1: Descriptions of Test Methods

1. TRICLOSAN Content: Determination of TRICLOSAN in Polyglactin 910 sutures

The sample preparation and assay are accomplished by extraction of triclosan from the sutures. Quantification of triclosan in the extract is conducted by High Performance Liquid Chromatography (HPLC).

2. Coating Add-on: Determination of Total Weight of Coating Material on a Suture An analytical test method was previously developed for the determination of total weight of coating material on a suture product. The sample preparation is accomplished by extraction of coating material by chloroform and quantification is conducted by gravimetric analysis.

Coating add on is calculated as follows:

$$\% \text{ total coating} = [(\text{Initial weight} - \text{Final weight})/\text{Initial weight}] \times 100$$

3. Measurement of Zone of Inhibition (ZOI)

A 5 cm section of an antibacterial suture is placed in a petri dish and inoculated with $1–5 \times 10^6$ CFU/ml of *E. cloacae* (ATCC 13047) to achieve a final concentration of $1–5 \times 10^5$ CFU of bacteria in the plate. Appropriate volumes of TSA medium will be added and mixed with the inoculum in the plate. After 18-24 hours of incubation, the in vitro efficacy of the sterilized antibacterial suture against the test organism is assessed by measuring the inhibition zone produced in the plate that surrounds the antibacterial suture.

The zone of inhibition is measured using a digital caliper. The shortest perpendicular distance will be measured at 3 locations on the suture (center & 2 end-points) from the edge of the suture to the edge of the confluent bacterial growth. The 3 measurement values are then averaged to obtain the final zone measurement. A zone of inhibition is not present if the measurement is smaller than 1.0 mm.

4. Method for Determining and Quantifying In Vitro Bacterial Attachment to Suture (Log Reduction)

The log attachment assay is conducted in a serum-supplemented medium (SST), which is consisted of serum, saline or (phosphate buffer) and TSB medium. Different levels of serum can be used to modify the challenge level of the test. In general, the higher the serum content in the growth medium, the lower the efficacy of the antimicrobial. Briefly, 10 cm of suture test article is placed in a well-plate after which 2 mL of SST medium inoculated with approximately $1–5 \times 10^5$ CFU/ml of *E. cloacae* (ATCC 13047) will be added to the well. The well-plate is incubated for a desired duration (typically 24 h) at 37° C. with shaking at 60 rpm.

After completion of the incubation period, the suture is retrieved and placed in a neutralizing buffer and sonicated to dissociate bacteria attached to the test article. The bacterial suspensions are subsequently plated and the CFU per device for the test samples are compared to the CFU per device of the control samples, which is then reported as log difference/reduction.

Example 2: Procedure of Sample Production, Including Methods of Triclosan Introduction

Illustrative Example 2A: Coating Process with Application of Antibacterial Agent Via the Coating Solution; Other Coating Components and Concentrations can be Used A spool of braid was placed on a let off and the braid was threaded through the coating line guides, and coating bath, a drying tunnel guides, the godet and finally a take up spool. The coating bath was filled with the coating solution, which contained 89% ethyl acetate solvent, 4.5% PG370 coating copolymer, 2% triclosan (the antibacterial agent) and 4.5% calcium stearate. The braided line was drawn off the take up, through the guides in the coating bath where it was coated. The coated braid was then drawn through the drying tunnel, where the ethyl acetate solvent evaporated off the braid leaving the copolymer, triclosan and calcium stearate on the braid. The coated, dried braid was wound onto a take up spool. The material was tested for coating amount and sent for cutting and, if desired, needle attachment. After the needle is attached to the strand it was wound into an inner package, placed into an outer foil package, and sterilized.

Illustrative Example 2B: Application of Antibacterial Agent Via Vapor Deposition Material was coated in the same manner as described in illustrative example 2A, however triclosan was not included in the coating solution. After coating the material was cut into strands and, if desired, a needle was attached. The needled strand was wound into an inner package of polymer or paper. A Tyvek patch was used as a reservoir to hold triclosan. The triclosan was solubilized in a solvent and precisely measured to 3 mg and applied to the patch. The patch was placed on the underside of the paper lid of the polymer tray inner package or on the flap of the paper inner package. The assembly was placed into the outer package (foil) and sterilized and vacuum dried. Alternatively, in the case of plastic packages, the triclosan can be embedded in the plastic itself and no patch is required. This process used elevated temperature and vacuum and this process vaporized the triclosan off the patch and onto the suture (VAPOR Process).

Example 3: Quantitative Knot Slide Test

Sterile antimicrobial sutures are removed from the package and cut to a length of 14 inches. The 14-inch strand of suture is placed in water for 60 seconds to simulate in vivo conditions. Subsequently, a square knot is tied around a cylindrical fixture with a diameter of 2 inches. The ends of the suture with the square knot and 2-inch diameter loop is fixated in the fixtures of an Instron with a gauge length of 2 inches. The tensile test is executed at a speed of 20 inches per minute. In order to determine the work required to slide and close the knot, the area under the curve up to the onset of the peak associated with the breaking of the closed suture is integrated and normalized to the extension to adjust for any differences in braid elasticity and reported as a knot slide in N/m. Less than 60 N/m is considered acceptable (i.e., non-locking) suture handling; lower than 30 N/m is preferred for smooth knot formation.

Example 4: Example of Achievable Triclosan Content on Sutures Coated with PG370/Calcium Stearate/Triclosan The current process for antimicrobial braided sutures introduces the antimicrobial agent during the coating pro-

Figure 2:
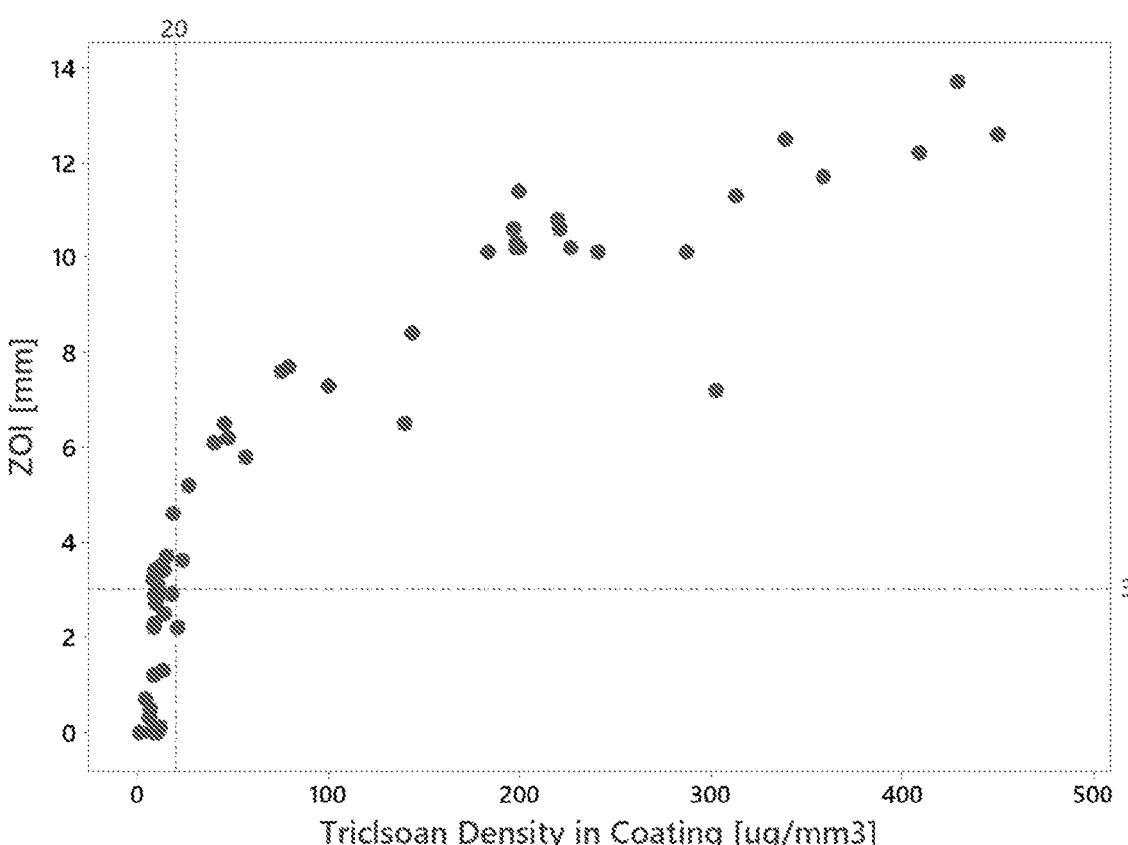
FIG. 2 illustrates the relationship between Zone of inhibition after 24 hours and triclosan density in the coating for PG370/calcium stearate coatings.

Example 5: Example of Anti-Microbial Efficacy and Suture Handling Properties of USP Size 2-0 Suture Coated with PG370/Calcium Stearate Prepared with the Triclosan Vapor Process Significantly higher triclosan content on the suture can be achieved when triclosan is introduced using the vapor process. Table 2 and FIG. 2 show that consistent average ZOI against *E. cloacae* larger than 3 mm can be obtained when the triclosan density in the coating is greater than about $(+/-2.5 \ \mu g/mm^3)$ 20 $\mu g/mm^3$. Accounting for the fact that about half of the coating does not accommodate triclosan in a meaningful manner, the effective triclosan density in the triclophilic component needs to be greater than about $(+/-5 \ \mu g/mm^3)$ 40 $\mu g/mm^3$.

TABLE 2

| PG370 in Coating Solution (wt %) | CaSt in Coating Solution (wt %) | Triclosan Reservoir Dose (mg) | PG370 (wt % to suture) | Triclosan Content (ug/m) | Triclosan Density in Coating (ug/mm³) | ZOI (mm) | Package |
|---|---|---|---|---|---|---|---|
| 6 | 6 | 3.2 | 1.95 | 42 | 13 | 1.3 | Plastic |
| 3 | 3 | 6 | 0.7 | 20 | 18 | 2.2 | Plastic |
| 6 | 6 | 5.8 | 1.95 | 84 | 27 | 5.2 | Plastic |
| 3 | 3 | 2 | 1.09 | 58 | 48 | 5.6 | Paper |
| 6 | 6 | 2 | 1.75 | 135 | 52 | 6.3 | Paper |
| 6 | 6 | 2 | 1.7 | 161 | 57 | 7.2 | Paper |
| 4.5 | 4.5 | 2 | 1.58 | 108 | 55 | 7.3 | Paper | cess. When sutures prepared as described in Example 2A and supplying the triclosan in the coating solution, a limited triclosan content can be obtained (table 1). Utilizing a typical suture coating system (4.5 wt. % PG370/4.5 wt. % CaSt with 2 wt. % triclosan in the coating solution) a maximum of about 16 μg/m can be achieved in plastic suture packages, whereas about 31 μg/m can be achieved in a paper suture package. Increasing the triclosan content solution to 5 wt. %, results in a triclosan content on the suture of 93 μg/m. Even increasing the coating solution concentration to the maximum practical concentration for a functional suture (6 wt. % PG370/6 wt. % CaSt with 5 wt. % triclosan in coating) results in a triclosan content on suture of about 112 ug/m.

TABLE 1

| USP Size | PG370 in Coating Solution (wt %) | CaSt in Coating Solution | Triclosan in Coating Solution (wt %) | Triclosan Content (ug/m) | Package |
|---|---|---|---|---|---|
| 2-0 | 4.5 | 4.5 | 2 | 16 | Plastic |
| 2-0 | 4.5 | 4.5 | 2 | 31 | Paper |
| 2-0 | 4.5 | 4.5 | 5 | 93 | Paper |
| 2-0 | 6 | 6 | 5 | 112 | Paper |

However, Table 3 shows that for a given coating, when Triclosan Content is increased, the suture handling properties starts to deteriorate to the point of being non-functional. Table 4 shows that the handling properties at a given Triclosan Content can be improved by increasing the calcium stearate content in the coating.

TABLE 3

| PG370 in Coating Solution (wt %) | CaSt in Coating Solution (wt %) | Triclosan Reservoir Dose (mg) | Coating Add-on (%) | Triclosan Content (ug/m) | Knot Slide (N/m) | Package |
|---|---|---|---|---|---|---|
| 4.5 | 4.5 | 4 | 2.28 | 27 | 18.3 | Plastic |
| 4.5 | 4.5 | 7.4 | 2.00 | 46 | 54.5 | Plastic |
| 4.5 | 4.5 | 7.4 | 2.00 | 734 | 109* | Paper |

*5 of 10 samples locked and broke during test

TABLE 4

| PG370 in Coating Solution (wt %) | CaSt in Coating Solution (wt %) | Triclosan Reservoir Dose (mg) | Triclosan Content (ug/m) | Knot Slide (N/m) | Package |
|---|---|---|---|---|---|
| 4.5 | 2 | 4 | 332 | 187.1 | Paper |
| 4.5 | 4.5 | 4 | 314 | 43.6 | Paper |
| 4.5 | 7 | 4 | 335 | 31.1 | Paper |

Table 5 shows some extreme combinations of calcium stearate-to-PG370 ratios and coating thickness that result in sutures that both have good antimicrobial properties and suture handling properties.

TABLE 5

| PG370 in Coating Solution (wt %) | CaSt in Coating Solution (wt %) | Triclosan Reservoir Dose (mg) | PG370 Add-on (%) | Triclosan Content (ug/m) | E. cloacae ZOI (mm) | Knot Slide (N/m) | Package |
|---|---|---|---|---|---|---|---|
| 3 | 3 | 6 | 0.66 | 20 | 2.9 | 38.2 | Plastic |
| 3 | 6 | 6 | 0.62 | 21 | 3.5 | 13.0 | Plastic |
| 6 | 6 | 6 | 1.65 | 43 | 3.7 | 16.9 | Plastic |
| 7 | 4.5 | 4 | 1.50 | 417 | 10.2 | 37.7 | Paper |

ZOI

Efficacy can be achieved using a coating combination of NVC and PG370. Table 6 below shows some examples having different coating ratios and triclosan delivery methods. As can be seen, significantly higher triclosan content on the suture can be achieved for this coating combination of NVC and PG370 with either delivery method compared to the coating system described in examples 4 and 5. Still higher triclosan content on the suture can be achieved with the vapor method compared to the triclosan-in-the-coating method. Note that all conditions provide suture handling properties in the most preferred range despite the significantly higher Triclosan Content than described in example 5.

Figure 3:
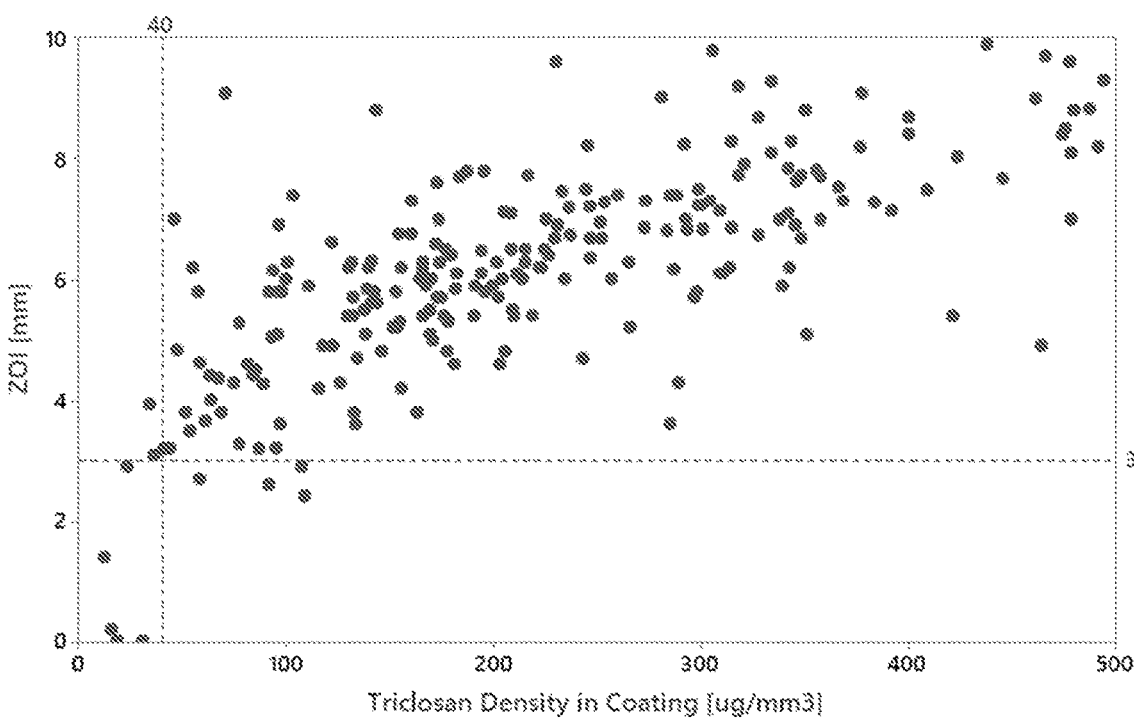
FIG. 3 illustrates the relationship between Zone of inhibition after 24 hours and triclosan density in the coating for NVC based coatings.

In order to have sufficient ZOI against E. cloacae, a certain minimum Triclosan Content is essential. However, the Triclosan Density in the coating needs to be such that elution of the antimicrobial agent to the environment is sufficiently fast. Table 6 shows samples demonstrating favorable ZOI for E. cloacae with triclosan at about (+/−10 µg/m) 100 µg/m, more preferably above about 150 µg/m, whereas samples below 100 µg/m do not exhibit sufficient ZOI. In addition, FIG. 3 shows that in order to obtain consistently favorable ZOI (>3 mm) for E. cloacae for samples with about 100 µg/m triclosan, the Triclosan Density needs to exceed about (+/−5 µg/mm$^3$) 40 µg/mm$^3$.

TABLE 6

| NVC in Coating Solution (wt %) | PG370 in Coating Solution (wt %) | Triclosan Reservoir Dose | Coating Add-On (wt %) | Triclosan Content (ug/m) | Triclosan Density in Coating (ug/mm$^3$) | E. cloacae Baseline ZOI (mm) | Package |
|---|---|---|---|---|---|---|---|
| 4 | 2 | 0.8 mg | 1.35 | 21 | 18 | 0 | Plastic |
| 8 | 4 | 0.8 mg | 3.15 | 42 | 16 | 0.2 | Plastic |
| 5 | 0 | 3% in coating | 1.31 | 45 | 40 | 2.9 | Paper |
| 5.25 | 0 | 1.0 mg | 1.29 | 58 | 53 | 0 | Plastic |
| 5.25 | 3.75 | 1.0 mg | 2.39 | 63 | 31 | 0 | Plastic |
| 8 | 4 | 0.5 mg | 3.15 | 109 | 41 | 3.2 | Plastic |
| 5.25 | 3.75 | 1.0 mg | 2.39 | 124 | 61 | 3.7 | Plastic |
| 3.9 | 6 | 2.4 mg | 3.17 | 144 | 53 | 3.5 | Plastic |
| 6 | 0 | 5% in coating | 1.57 | 228 | 170 | 4.9 | Paper |
| 5.25 | 3.75 | 1 mg | 2.39 | 273 | 133 | 3.6 | Paper |
| 3.9 | 6 | 2.4 mg | 3.17 | 300 | 111 | 5.9 | Plastic |
| 5.25 | 3.75 | 8 mg | 2.39 | 997 | 487 | 8.8 | Plastic |

Table 7 shows that sutures of different USP sizes behave similarly to USP size 2-0 sutures. The smallest density observed for USP size 1 was 41 µg/mm$^3$ resulting in an average ZOI of 4.2 mm. For USP size 4-0, insufficient average ZOI is obtained when Triclosan Density in coating is below about (+/−5 µg/mm$^3$) 40 µg/mm$^3$, while sufficient is obtained when Triclosan Density is greater than about 40 µg/mm$^3$.

TABLE 7

| USP size | NVC in Coating Solution (wt %) | PG370 in Coating Solution (wt %) | Triclosan Reservoir Dose (mg) | Coating Add On (wt %) | Triclosan Content (ug/m) | Triclosan Density in Coating (ug/mm$^3$) | E. cloacae Baseline ZOI (mm) | Package |
|---|---|---|---|---|---|---|---|---|
| 1 | 5 | 3 | 0.5 | 1.7 | 186 | 41 | 4.2 | Paper |
| 4-0 | 8 | 6 | 0.5 | 4.7 | 63 | 37 | 2.3 | Plastic |
| 4-0 | 10 | 5 | 1.0 | 5.1 | 173 | 95 | 3.7 | Plastic |

Example 7: Example of Suture Coated with NVC
and Optionally PG370 with Reduction in
Colonization of *E. cloacae* Against Control Suture A series of Log Reduction experiments was performed to evaluate the reduction in bacterial attachment to the antimicrobial suture (in the presence of 20% serum) versus an Ethicon Coated VICRYL Suture control. Examples are shown in table 8 for USP size 2-0 sutures with good (defined as >3 log in 20% serum) and poor *E. cloacae* log reduction.

As can be seen, a Triclosan Content on the suture greater than about (+/−10 ug/m) 150 µg/m is required to consistently obtain greater than 3 log reduction in attached bacteria against the control suture. Moreover, it can be seen that composition of the coating influenced the magnitude of the reduction once the previous criteria are met.

TABLE 8

| NVC in Coating Solution (wt %) | PG370 in Coating Solution (wt %) | Triclosan Reservoir Dose (mg) | Triclosan Content (ug/m) | *E. cloacae* Log Reduction | Package |
|---|---|---|---|---|---|
| 5.25 | 3.75 | 1 | 63 | 0.5 | Plastic |
| 3.9 | 0 | 2.4 | 96 | 0.1 | Plastic |
| 5.25 | 3.75 | 1 | 124 | 2.8 | Plastic |
| 3.9 | 6 | 2.4 | 144 | 2.9 | Plastic |
| 6.6 | 6 | 2.4 | 171 | 3.6 | Plastic |
| 3 | 3.75 | 4.5 | 194 | 5 | Plastic |

TABLE 8-continued

| NVC in Coating Solution (wt %) | PG370 in Coating Solution (wt %) | Triclosan Reservoir Dose (mg) | Triclosan Content (ug/m) | *E. cloacae* Log Reduction | Package |
|---|---|---|---|---|---|
| 6.6 | 1.5 | 2.4 | 218 | 4.6 | Plastic |
| 3.9 | 6 | 2.4 | 252 | 5.2 | Plastic |
| 5.25 | 3.75 | 1 | 273 | 4.8 | Paper |
| 3.9 | 6 | 2.4 | 300 | 5.4 | Plastic |
| 6.6 | 0 | 2.4 | 323 | 4.8 | Plastic |
| 3.9 | 6 | 6.6 | 341 | 5.6 | Plastic |
| 6.6 | 6 | 2.4 | 381 | 3.8 | Plastic |

Example 8: Example of Suture Coated with NVC
and Optionally PG370 with Acceptable Suture
Handling Properties Table 9 shows suture handling properties for USP size 2-0 braided sutures. For acceptable suture handling, the knot-slide values need to be below about (+/−5 N/m) 60 N/m for this suture size. Preferably knot-slide is below 30 N/m, and for the more preferable sutures, it should be below 20 N/m in the test method described in example 3.

As can be seen in the table 9, Triclosan Density is the critical parameter for suture handling properties. For functional sutures, Triclosan Density should not exceed about (+/−20 µg/mm³) 1000 ug/mm³. More preferably, Triclosan Density should be below about 400 µg/mm³, and for more preferable performance, below about 300 µg/mm³.

TABLE 9

| USP Size | NVC in Coating Solution (wt %) | PG370 in Coating Solution (wt %) | Triclosan Reservoir Dose (mg) | Coating Add-On (wt %) | Triclosan Content (ug/m) | Triclosan Density in Coating (ug/mm³) | Knot-Slide (N/m) | Package |
|---|---|---|---|---|---|---|---|---|
| 2-0 | 6.6 | 6 | 2.4 | 3.43 | 171 | 58 | 13.4 | Plastic |
| 4-0 | 12 | 6 | 1.6 | 6.71 | 179 | 74 | 17.3 | Plastic |
| 2-0 | 3.9 | 6 | 2.4 | 3.17 | 300 | 111 | 16.4 | Plastic |
| 2-0 | 7.5 | 3 | 1 | 2.52 | 296 | 137 | 18.5 | Paper |
| 2-0 | 6 | 2 | 0 | 1.97 | 341 | 202 | 9.5 | Plastic |
| 2-0 | 6 | 0 | 0 | 1.57 | 382 | 283 | 14.9 | Plastic |
| 2-0 | 3 | 3.75 | 4.5 | 1.71 | 421 | 287 | 15.2 | Plastic |
| 2-0 | 5.25 | 3.75 | 4.5 | 2.39 | 591 | 289 | 15.5 | Plastic |
| 2-0 | 4.5 | 4.5 | 12 | 3.01 | 801 | 311 | 20.2 | Plastic |
| 2-0 | 8 | 4 | 0 | 3.15 | 882 | 327 | 24.6 | Plastic |
| 2-0 | 6.6 | 6 | 6.6 | 3.43 | 1029 | 350 | 26 | Plastic |
| 2-0 | 5.25 | 7.5 | 3.5 | 3.37 | 1263 | 438 | 35.5 | Paper |
| 2-0 | 6 | 6 | 4 | 3.19 | 1665 | 610 | 42.5 | Paper |
| 2-0 | 5.25 | 3.75 | 3.5 | 2.39 | 1468 | 717 | 34.7 | Paper |
| 2-0 | 6.6 | 6 | 5 | 3.43 | 2260 | 755 | 46.6 | Paper |
| 2-0 | 5.25 | 0 | 3.5 | 1.29 | 1288 | 1115 | 69.4 | Paper |
| 4-0 | 6 | 3 | 6 | 2.2 | 1356 | 1714 | 202.5 | Paper |

USP size 1 and 2 braids have a different braid construction, resulting in higher intrinsic friction compared to USP size 0 and below. For size 1, the acceptable threshold is below about (+/−5 N/m) 85 N/m, more preferably below about 55 N/m, and the more preferable handling are below about 45 N/m. For size 2, the acceptable threshold is below about (+/−5 N/m) 130 N/m, preferably below about 100 N/m, and the more preferable handling are below about 90 N/m. Table below shows that for suture handling properties similar dependencies on Triclosan Density exists for USP size 1 and 2 sutures.

TABLE 10

| USP Size | NVC in Coating Solution (wt %) | PG370 in Coating Solution (wt %) | Triclosan Reservoir Dose (mg) | Coating Add-On (wt %) | Triclosan Content (ug/m) | Triclosan Density in Coating (ug/mm$^3$) | Knot-Slide (N/m) | Package |
|---|---|---|---|---|---|---|---|---|
| 1 | 6 | 2 | 0.5 | 1.68 | 106 | 34 | 19.4 | Plastic |
| 1 | 6 | 2 | 2.1 | 1.81 | 356 | 106 | 36.6 | Plastic |
| 1 | 6 | 2 | 2.1 | 1.81 | 472 | 141 | 46.4 | Plastic |
| 2 | 4 | 2 | 2.1 | 1.27 | 468 | 137 | 56.2 | Plastic |
| 2 | 4 | 2 | 9.7 | 1.28 | 1502 | 438 | 94.8 | Plastic |

The importance of coating thickness in relation to Triclosan Content is highlighted in the table 11 (below). At similar Triclosan Content and at similar Triclosan Density, a certain minimum coating thickness is required to have non-locking sutures. For the thinnest coatings, the minimal thickness limits how much triclosan can be incorporated before inadequate handling properties occur.

coating system described in example 5. As can be seen at a Triclosan Content on the suture of about 300 ug/m, about 3 times lower knot-slide values are obtained for the NVC-based coating system. Moreover, at about 750 ug/m, the CaSt/PG370 based coating system results in unacceptable

TABLE 11

| USP Size | NVC in Coating Solution (wt %) | PG370 in Coating Solution (wt %) | Triclosan Reservoir Dose (mg) | Coating Add-on (%) | Coating Thickness (um) | Triclosan Content (ug/m) | Triclosan Density in Coating (ug/mm$^3$) | Locking sutures (%) | Knot Slide (N/m) | Package |
|---|---|---|---|---|---|---|---|---|---|---|
| 2-0 | 3.9 | 0 | 6.6 | 0.75 | 0.62 | 424 | 660 | 0 | 8.6 | Plastic |
| 2-0 | 3 | 0 | 4.5 | 0.66 | 0.54 | 369 | 653 | 50 | 29.5 | Plastic |
| 2-0 | 3 | 0 | 5 | 0.66 | 0.54 | 198 | 350 | 0 | 5.2 | Plastic |
| 4-0 | 6 | 2 | 1 | 2.07 | 1.10 | 57 | 77 | 50 | 14.5 | Plastic |
| 4-0 | 8 | 6 | 0.5 | 4.7 | 2.48 | 63 | 38 | 0 | 14.8 | Plastic |

The effect of NVC/PG370 ratio on suture handling properties is illustrated in table 12. As can be seen, at a similar Triclosan Content on the suture and Triclosan Density, knot slide improves (decreases) as the NVC/PG370 ratio increases.

suture handling (about 50% of the tested suture locked up), whereas the NVC-based coating system still demonstrates preferrable knot-slide values. The addition of NVC to the PG370/CaSt coating system significantly improves suture handling compared to the PG370/CaSt alone.

TABLE 13

| PG370 in Coating Solution (wt %) | NVC in Coating Solution (wt %) | CaSt in Coating Solution (wt %) | Triclosan Reservoir Dose (mg) | Coating Add-on (%) | Triclosan Content (ug/m) | Knot Slide (N/m) | Package |
|---|---|---|---|---|---|---|---|
| 3.75 | 5.25 | 0 | 1 | 2.39 | 273 | 11.7 | Paper |
| 4.5 | 3 | 4.5 | 4.5 | 3.0 | 377 | 21.2 | Plastic |
| 4.5 | 0 | 4.5 | 7 | 1.99 | 335 | 31.1 | Paper |
| 6 | 6.6 | 0 | 2 | 3.43 | 778 | 30.1 | Paper |
| 4.5 | 0 | 4.5 | 7.4 | 2.00 | 734 | 109* | Paper |

*5 of 10 samples locked and broke during test

TABLE 12

| USP Size | NVC in Coating Solution (wt %) | PG370 in Coating Solution (wt %) | Total Add-On (%) | Triclosan Content (ug/m) | Knot-Slide (N/m) | Triclosan Density in Coating (ug/mm$^3$) |
|---|---|---|---|---|---|---|
| 2-0 | 7 | 4 | 2.89 | 341 | 22.2 | 138 |
| 2-0 | 7 | 3 | 2.89 | 351 | 17.3 | 142 |
| 2-0 | 7 | 2 | 2.58 | 333 | 15.5 | 151 |

Table 13 shows a comparison of suture handling properties of NVC-based coating systems versus the PG370/CaSt

Example 9: Extended Zone of Inhibition Experiments

To evaluate prolonged antimicrobial efficacy of the antimicrobial sutures, a repeated Zone of Inhibition (ZOI) experiment was performed. Briefly, a ZOI experiment as described in Example 3 was performed but after 24 hours, the suture was retrieved from the assay and plated in a fresh agar plate with fresh bacterial inoculum. This approach was repeated for 3 days.

Figure 4:
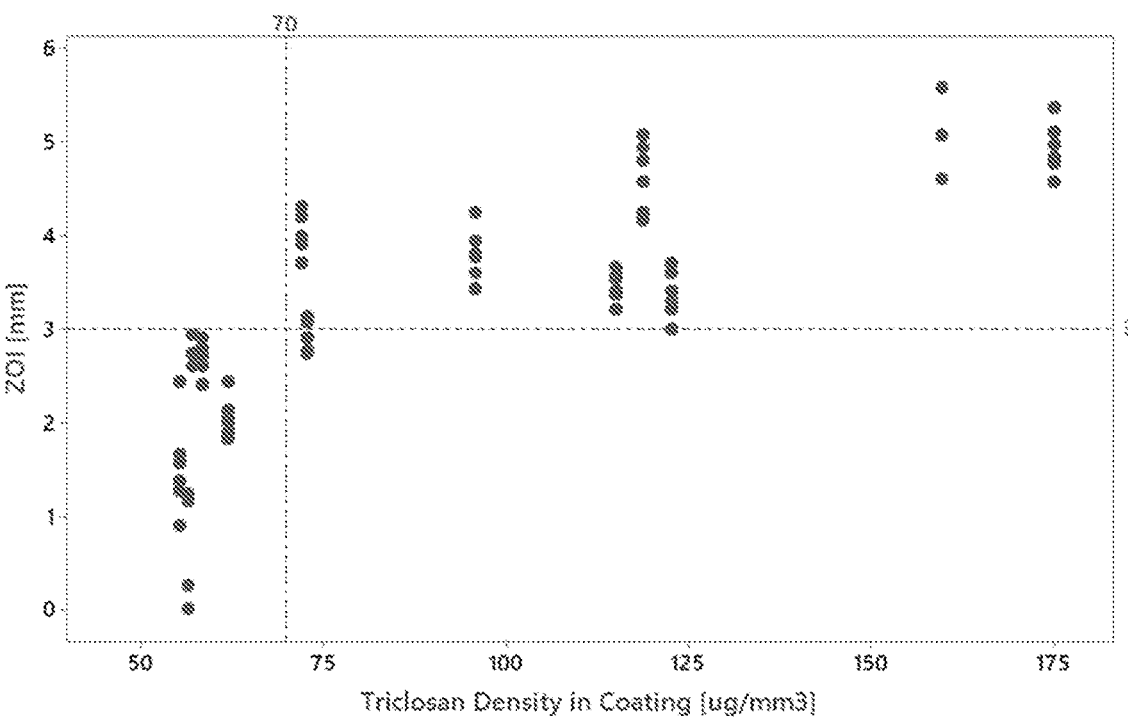
FIG. 4 illustrates the relationship between Zone of inhibition after 72 hours (3 days) and triclosan density in the coating for NVC based coatings.

Various suture sizes, triclosan introduction methods and package types were evaluated. The table below (table 14) reports the average ZOI in mm at day 3. As can be seen in FIG. 4, sufficient average ZOI greater than and about 3 mm are obtained when the triclosan density in the coating exceeds about (+/−5 ug/mm$^3$) 70 ug/mm$^3$.

TABLE 14

| USP Size | NVC in Coating Solution (wt %) | PG370in Coating Solution (wt %) | Triclosan Reservoir Dose (mg) | Triclosan Content (ug/m) | Triclosan Density in Coating (ug/mm$^3$) | *E. cloacae* ZOI Baseline (mm) | Day 3 (mm) | Package |
|---|---|---|---|---|---|---|---|---|
| 4-0 | 8.00% | 4.00% | 1.6 | 79 | 55 | 3.7 | 1.5 | Plastic |
| 2-0 | 4.00% | 2.00% | 1.6 | 65 | 57 | 3.8 | 0.7 | Plastic |
| 2-0 | 8.00% | 4.00% | 1.6 | 157 | 58 | 3.7 | 2.7 | Plastic |
| 4-0 | 12.00% | 6.00% | 1.6 | 175 | 73 | 3.5 | 3 | Plastic |
| 1 | 6.00% | 2.00% | 1.6 | 179 | 81 | 4.1 | 2.8 | Plastic |
| 2-0 | 6.00% | 2.00% | 2.3 | 171 | 96 | 5.8 | 3.8 | Plastic |
| 1 | 6.00% | 2.00% | 2.3 | 226 | 103 | 5 | 4 | Plastic |
| 4-0 | 8 | 4 | 8.25 | 162 | 115 | 4.5 | 3.5 | Plastic |
| 2-0 | 8.00% | 4.00% | 3.2 | 320 | 119 | 4.2 | 4.6 | Plastic |
| 2-0 | 6.00% | 2.00% | 2.5 | 269 | 160 | 4 | 5.1 | Plastic |
| 2-0 | 4.00% | 2.00% | 4.2 | 202 | 175 | 5.1 | 4.9 | Plastic |

Example 10: Extended Anti-Colonization Experiments

To evaluate prolonged antimicrobial efficacy of the antimicrobial sutures, a repeated anti-colonization (log attachment) experiment was performed. Three identical well-plates (containing 10 cm cut sutures) were prepared. The attachment studies were done with *E. cloacae* in SST (5% serum).

On the first day, one well-plate was inoculated with the test organism at 1-5×10^5 CFU/ml in SST (5% serum) and processed per the standard log attachment procedure as described in example 1; whereas the other two plates only received SST (5%) and remained uninoculated. Each subsequent day, one of the plates was inoculated and processed as per the standard log attachment procedure until all plates were processed.

Various suture sizes, triclosan introduction methods and package types were evaluated. The tables below report the average log reduction compared to the control suture. Table 15 shows results of selected samples that were tested after two days. As can be seen, when initial (day 0) total triclosan content on the suture exceeds about (+/−10 ug/m) 200 ug/m, a 3 log reduction in colonization against the control suture can be achieved for two days. Table 16 shows results of selected samples that were tested after three days. As can be seen, in this scenario, not only does the initial total triclosan content on the suture need to exceed about 300 ug/m, the coating thickness needs to be greater than 2 micron, more preferably 2.5 micron, to sustain a 3 log reduction in colonization against the control suture.

TABLE 15

| USP Size | NVC in Coating Solution (wt %) | PG370 in Coating Solution (wt %) | CaSt in Coating Solution (wt %) | Triclosan Reservoir Dose (mg) | Initial Triclosan Content (ug/m) | Triclosan Density in Coating (ug/mm$^3$) | *E. cloacae* Log Difference – Day 2 | Package |
|---|---|---|---|---|---|---|---|---|
| 2-0 | 0 | 4.5 | 4.5 | 0.6 | 21 | 12 | 0.28 | Paper |
| 2-0 | 0 | 6 | 6 | 6 | 60 | 21 | 0.22 | Plastic |
| 4-0 | 8 | 4 | 0 | 1.6 | 78 | 55 | 0.42 | Plastic |
| 2-0 | 4 | 2 | 0 | 2.1 | 142 | 123 | 0.90 | Plastic |
| 2-0 | 8 | 4 | 0 | 1.6 | 158 | 59 | 0.89 | Plastic |
| 2-0 | 8 | 4 | 0 | 3.2 | 320 | 119 | 3.24 | Plastic |
| 2-0 | 6 | 2 | 0 | 2.5 | 269 | 160 | 3.96 | Plastic |

TABLE 16

| USP Size | NVC in Coating Solution (wt %) | PG370 in Coating Solution (wt %) | CaSt in Coating Solution (wt %) | Initial Triclosan Content (ug/m) | Coating Thickness (um) | *E. cloacae* Log Difference – Day 3 | Package |
|---|---|---|---|---|---|---|---|
| 2-0 | 4 | 2 | 0 | 402 | 1.1 | 1.0 | Plastic |
| 2-0 | 6 | 2 | 0 | 335 | 1.7 | 1.0 | Plastic |
| 2-0 | 8 | 4 | 0 | 321 | 2.6 | 3.5 | Plastic |
| 1 | 6 | 4 | 0 | 417 | 2.7 | 3.9 | Plastic |
| 1 | 5 | 4 | 0 | 350 | 2.5 | 3.7 | Plastic |

23

We claim:

1. A coated medical device comprising at least one implantable segment having a coating of:

an effective amount of triclosan; and b. A triclophilic component that is lubricious or a triclophilic component and a lubricious component, or combinations thereof;

wherein (i) the amount of triclosan is between about 150 micrograms per meter and about 2500 micrograms per meter, and (ii) the coating is substantially homogeneous and has a density in the coating of triclosan between about 40 micrograms per cubic millimeter ($\mu g/mm^3$) and about 1000 $\mu g/mm^3$.

2. A coated medical device of claim 1 wherein the triclophilic component is lubricious.

3. A coated medical device according to claim 1 that is a braided suture and has a suture coating in which the amount of triclosan exceeds 150 $\mu g$ (micrograms) per meter of suture ($\mu g/m$), has a triclosan density in the triclophilic components greater than about 40 $\mu g/mm^3$, and consistently sustains at least 3 millimeters (mm) Zone of Inhibition against *E. cloacae* at 24 hours.

4. A coated medical device according to claim 3 that is a suture having a USP size 2 through 3/0 and the weight percent of the coating to suture weight is between 0.5% and 8%.

5. A coated medical device according to claim 3 that is a suture having a USP size 4/0 and the weight percent of the coating to suture weight is between 4% and 10%.

6. A coated medical device according to claim 1 that is a braided suture and has a suture coating in which the amount of triclosan exceeds 100 $\mu g$ (micrograms) per meter of suture (ug/m), has a triclosan density in the triclophilic components greater than about 40 $\mu g/mm^3$, and consistently sustains at least 3 millimeters (mm) Zone of Inhibition against *E. cloacae* at 24 hours.

7. A coated medical device according to claim 1 that is a braided suture and has a suture coating in which the amount of triclosan exceeds 150 $\mu g/m$ of suture and sustains at least 3 mm Zone of Inhibition against *E. cloacae* for at least 3 days.

8. A coated medical device according to claim 7 that is a braided suture and has a suture coating in which the triclosan density in the coating exceeds 70 ug/mm³, and sustains at least 3 mm Zone of Inhibition against *E. cloacae* for at least 3 days.

9. A coated medical device according to claim 1 that is a braided suture and has a suture coating in which the amount of triclosan exceeds about 150 $\mu g/m$ and reduces bacterial attachment of *E. cloacae* with at least one 3 log reduction in 20% Serum:Saline:Tryptic soy Broth (TSB) (SST) containing media relative to a non-triclosan containing suture of the same chemical nature, architecture and size.

10. A coated medical device according to claim 1 that is a braided suture and has a suture coating in which the amount of triclosan exceeds 200 $\mu g/m$ of suture, and sustains at least 3 log reduction against *E. cloacae* in 5% SST containing media relative to a non-triclosan containing suture of the same chemical nature, architecture and size for at least 2 days.

11. A coated medical device according to claim 1 that is a braided suture and has a suture coating in which the amount of triclosan exceeds 300 $\mu g/m$ of suture and wherein coating thickness exceeds about 2 micrometer ($\mu m$), and

24 sustains at least 3 log reduction against *E. cloacae* in 5% SST containing media relative to a non-triclosan containing suture of the same chemical nature, architecture and size for at least 3 days.

12. A coated medical device according to claim 1 that is a suture having a suture USP size between and including sizes 0 to 4/0 that is braided and a quantitative knot slide value of less than 60 N/m.

13. A coated medical device according to claim 1 that is a suture having a suture USP size between and including sizes 0 to 4/0 that is braided wherein the triclosan density in the coating is less than about 1000 ug/mm³.

14. A coated medical device according to claim 1 that is a suture having a suture USP size 1 that is braided and a quantitative knot slide value of less than 85 N/m.

15. A coated medical device according to claim 1 that is a suture having a suture USP size 1 that is braided wherein the triclosan density in the coating is less than 400 ug/mm³.

16. A coated medical device according to claim 1 that is a suture having a suture USP size 2 that is braided and a quantitative knot slide value of less than 130 N/m.

17. A coated medical device according to claim 1 that is a suture having a suture USP size 2 that is braided wherein the triclosan density in the coating is less than 400 ug/mm³.

18. A coated medical device according to claim 1 that is a suture having a suture USP size between and includes sizes 2 to 4/0.

19. A coated medical device according to claim 1 that is a suture in the form of a coated, multifilament braid of polyglactin 910.

20. A coated medical device according to claim 1 wherein the triclophilic component is a coating of poly(e-caprolactone-co-glycolide) 90/10, poly(glycolide-co-lactide) 65/35, or combinations thereof.

21. A coated medical device according to claim 1 wherein the weight ratio of poly(glycolide-co-lactide) 65/35 to poly (e-caprolactone-go-glycolide) 90/10 is 0 to 1.0.

22. A coated medical device according to claim 1 that is a suture in a sealed package with antimicrobial agent on an interior surface or embedded within the material of the package.

23. A coated medical device according to claim 22 wherein the sealed package is made of polypropylene, high density polyethylene (HDPE), paper, or combinations thereof.

24. A coating solution for coating a medical device according to claim 1, or 2 which is a braided suture of USP size 2 through 3/0 comprising:

a. about 3 weight percent to at least about 8 weight percent of poly(e-caprolactone-co-glycolide) having a monomer ratio of caprolactone to glycolide of 90/10, and b. about 0 to about 6 weight percent of poly(glycolide-co-lactide) having a monomer ratio of glycolide to lactide of 65/35.

25. A coating solution according to claim 24 comprising:

a. from about 4 weight percent to about 8 weight percent of poly(e-caprolactone-co-glycolide) having a monomer ratio of caprolactone to glycolide of 90/10 and b. from about 0 to about 4 weight percent of poly (glycolide-co-lactide) having a monomer ratio of glycolide to lactide of 65/35.

26. A coating solution for coating a medical device according to claim 1, or 2 which is a braided suture of USP size 4/0 compromising:

a. about 8 weight percent to at least about 16 weight percent of poly(e-caprolactone-co-glycolide) having a monomer ratio of caprolactone to glycolide of 90/10, and b. about from 5 to 8 weight percent of poly(glycolide-co-lactide) having a monomer ratio of glycolide to lactide of 65/35.

27. A method of introducing triclosan into the medical device according to claim 1 wherein the medical device is a coated braided suture, by exposing the coated suture to patches having a reservoir of triclosan, wherein the transfer occurs under raised temperature and/or reduced pressure.

28. A method of introducing triclosan into the medical device according to claim 1 wherein the medical device is a coated braided suture, exposing the suture to a reservoir of triclosan located or embedded within dosed trays, wherein the transfer occurs under raised temperature and/or reduced pressure.

* * * * *